United States Patent
Petay et al.

(10) Patent No.: US 8,197,826 B2
(45) Date of Patent: Jun. 12, 2012

(54) IMMUNOMODULATORY PRODUCT OBTAINED FROM A BIFIDOBACTERIUM CULTURE AND COMPOSITIONS CONTAINING THE SAME

(75) Inventors: Valérie Petay, Nieppe (FR); Francis Lecroix, Godewaersvelde (FR); Emmanuel Perrin, Boescheppe (FR); Charles Gontier, Lille (FR); Jean-Pierre Blareau, Steenvoorde (FR); Marie-Bénédicte Romond, Lille (FR); Elisabeth Singer, Lille (FR); Marie-Françoise Odou, Godeswaersvelde (FR); Catherine Demailly-Mullie, Le Sars (FR)

(73) Assignee: Compagnie Gervais Danone (FR)

( * ) Notice: Subject to any disclaimer, the term of this patent is extended or adjusted under 35 U.S.C. 154(b) by 769 days.

(21) Appl. No.: 10/552,957

(22) PCT Filed: Apr. 8, 2004

(86) PCT No.: PCT/FR2004/000874
§ 371 (c)(1),
(2), (4) Date: Apr. 11, 2008

(87) PCT Pub. No.: WO2004/093898
PCT Pub. Date: Nov. 4, 2004

(65) Prior Publication Data
US 2008/0248056 A1    Oct. 9, 2008

(30) Foreign Application Priority Data

Apr. 16, 2003 (FR) ...................................... 03 04746
Mar. 26, 2004 (FR) ...................................... 04 03158

(51) Int. Cl.
*A61K 39/02* (2006.01)
*A61K 45/00* (2006.01)
*A61K 39/29* (2006.01)

(52) U.S. Cl. ............... 424/234.1; 424/278.1; 424/282.1; 424/184.1; 424/190.1

(58) Field of Classification Search ..................... None
See application file for complete search history.

(56) References Cited

U.S. PATENT DOCUMENTS

| | | | |
|---|---|---|---|
| 7,410,653 B1 * | 8/2008 | Blareau et al. | 424/520 |
| 2008/0038776 A1 * | 2/2008 | Romond et al. | 435/69.1 |
| 2008/0268099 A1 * | 10/2008 | Blareau et al. | 426/61 |

FOREIGN PATENT DOCUMENTS

| | | | |
|---|---|---|---|
| EP | 0 768 375 | | 4/1997 |
| WO | WO 01/01785 | * | 1/2001 |

OTHER PUBLICATIONS

International Search Report for PCT/FR2004/000874 filed Apr. 8, 2004.
Mullie C et al: "Partial characterization of bifidobacterium breve C50 cell-free whey compounds inducing modifications to the intestinal micoflora"; Journal of Dairy Science, American Dairy Science Association; Champaign, IL; vol. 85, No. 6, Jun. 2002, pp. 1383-1389; XP002269107.
Liepke Cornelia et al: "Human milk provides peptides highly stimulating the growth of bifidobacteria"; European Journal of Biochemistry; vol. 269, No. 2; Jan. 2002; pp. 712-718; XP002288966.
Yasui Hisako et al: "Protection against influenza virus infection of mice fed Bifidobacterium breve YIT4064"; Clinical and Diagnostic Laboratory Immunology; vol. 6, No. 2, Mar. 1999; pp. 186-192; XP002288967.

* cited by examiner

*Primary Examiner* — Vanessa L Ford
*Assistant Examiner* — Lakia Tongue
(74) *Attorney, Agent, or Firm* — Alston & Bird LLP (57) ABSTRACT

The invention relates to an immunomodulatory product obtained from a *Bifidobacterium* culture, to the use thereof, especially as a medicament or a food ingredient, and to pharmaceutical or food compositions containing the same.

25 Claims, 3 Drawing Sheets

SEQUENCE LISTING

<160> NUMBER OF SEQ ID NOS: 12

<210> SEQ ID NO 1
<211> LENGTH: 21
<212> TYPE: PRT
<213> ORGANISM: Bifidobacterium breve

<400> SEQUENCE: 1

Arg Glu Leu Gly Ile Gly Thr Pro Ser Phe Leu His Asn Gly Gly Gln
1               5                   10                  15

Trp Tyr Ile Tyr Ala
            20

<210> SEQ ID NO 2
<211> LENGTH: 13
<212> TYPE: PRT

```
<213> ORGANISM: Bifidobacterium breve
<220> FEATURE:
<221> NAME/KEY: MISC_FEATURE
<222> LOCATION: (10)..(10)
<223> OTHER INFORMATION: any amino acid

<400> SEQUENCE: 2

Arg Val Leu Tyr Asn Pro Gly Gln Tyr Xaa Tyr Val Arg
1               5                   10

<210> SEQ ID NO 3
<211> LENGTH: 22
<212> TYPE: PRT
<213> ORGANISM: Bifidobacterium breve

<400> SEQUENCE: 3

Glu Gln Ala Thr Ala Asn Gly Gln Val Ser Ser Gly Gln Gln Ser Thr
1               5                   10                  15

Gly Gly Ser Ala Ala Pro
            20

<210> SEQ ID NO 4
<211> LENGTH: 21
<212> TYPE: DNA
<213> ORGANISM: Artificial sequence
<220> FEATURE:
<223> OTHER INFORMATION: PCR primer

<400> SEQUENCE: 4
tcaatcatgg cctgtggtct g                                              21

<210> SEQ ID NO 5
<211> LENGTH: 19
<212> TYPE: DNA
<213> ORGANISM: Artificial sequence
<220> FEATURE:
<223> OTHER INFORMATION: PCR primer

<400> SEQUENCE: 5
aagctcttgg cgtccgagg                                                 19

<210> SEQ ID NO 6
<211> LENGTH: 24
<212> TYPE: DNA
<213> ORGANISM: Artificial sequence
<220> FEATURE:
<223> OTHER INFORMATION: oliognucleotide probe

<400> SEQUENCE: 6
tcgccagcaa cctgaatcaa cctg                                           24

<210> SEQ ID NO 7
<211> LENGTH: 19
<212> TYPE: DNA
<213> ORGANISM: Artificial sequence
<220> FEATURE:
<223> OTHER INFORMATION: PCR primer

<400> SEQUENCE: 7
aatggcagac agcttttcg                                                 19

<210> SEQ ID NO 8
<211> LENGTH: 18
<212> TYPE: DNA
<213> ORGANISM: Artificial sequence
<220> FEATURE:
<223> OTHER INFORMATION: PCR primer
```

```
<400> SEQUENCE: 8
gatcatggcg tggttagc                                                       18

<210> SEQ ID NO 9
<211> LENGTH: 30
<212> TYPE: DNA
<213> ORGANISM: Artificial sequence
<220> FEATURE:
<223> OTHER INFORMATION: oliognucleotide probe

<400> SEQUENCE: 9
ttccacttta acccccgctt caatgagaac                                          30

<210> SEQ ID NO 10
<211> LENGTH: 21
<212> TYPE: DNA
<213> ORGANISM: Artificial sequence
<220> FEATURE:
<223> OTHER INFORMATION: PCR primer

<400> SEQUENCE: 10
tggcgctttt gactcaggat t                                                   21

<210> SEQ ID NO 11
<211> LENGTH: 21
<212> TYPE: DNA
<213> ORGANISM: Artificial sequence
<220> FEATURE:
<223> OTHER INFORMATION: PCR primer

<400> SEQUENCE: 11
gggatgtttg ctccaaccaa c                                                   21

<210> SEQ ID NO 12
<211> LENGTH: 27
<212> TYPE: DNA
<213> ORGANISM: Artificial sequence
<220> FEATURE:
<223> OTHER INFORMATION: oliognucleotide probe

<400> SEQUENCE: 12
gccgtcgcct tcaccgttcc agttttt                                             27
```

IMMUNOMODULATORY PRODUCT OBTAINED FROM A BIFIDOBACTERIUM CULTURE AND COMPOSITIONS CONTAINING THE SAME

The present invention relates to a immunomodulatory product obtained from a *Bifidobacterium* culture, to the use thereof, in particular as a medicament or a food ingredient, and also to the pharmaceutical or food compositions containing it.

The *Bifidobacterium* genus is part of the family Actinomycetaceae; it includes strictly anaerobic Gram-positive bacilli that ferment glucose via the fructose 6-phosphate phosphoketolase pathway. Their optimal growth pH is between 6 and 7, and their optimal growth temperature is between 37 and 46° C.

Bifidobacteria are part of the normal human intestinal flora, and they are recognized as having many beneficial effects on health. It is in particular known that breast-fed infants, who possess an intestinal flora in which *bifidobacteria* predominate, are more resistant to infections and exhibit in particular a lower risk of diarrhea than infants fed with conventional industrial milk preparations.

The role of *bifidobacteria* in this increased resistance to infections has not been completely elucidated. Various studies indicate that they have an immunomodulatory capacity that is thought to involve polysaccharide substances associated with the bacterial wall, or secreted by the bacteria during anaerobic fermentation. Gomez et al. (FEMS Microbiol. Lett. 1988, 56, 47-52) describe the immunomodulatory effect of exocellular fractions rich in polysaccharides produced by *Bifidobacterium adolescentis*; patent application FR 2 652 590 describes an immunopotentiating exopolymer that is polysaccharide in nature, produced by a strain of the continuum *Bifidobacterium infantis longum*; Honoso et al. (Biosci. Biotech. Biochem., 1997, 61, 312-316 and Bioscience Microflora, 1998, 17, 97-104) describe immunopotentiating polysaccharides produced by various species of *Bifidobacterium*. The immunomodulatory action of *Bifidobacteria* also manifests itself through the regulation of the intestinal microflora, in particular to the detriment of the development of pathogenic bacterial species. Romond et al. (Anaerobe, 1997, 3, 137-143 and J. Dairy Sci., 1998, 81, 1229-1235) thus describe fractions rich in glycoproteins, produced by *Bifidobacterium breve* under anaerobic fermentation conditions, and induce, in vivo, a regulatory effect on the intestinal microflora.

Many products fermented by bifidobacteria, possibly combined with other lactic acid bacteria, and the ingestion of which makes it possible to benefit from the immunomodulatory effects of bifidobacteria and of their fermentation products, are thus found on the market.

However, and in the particular case of infant food, these products have the drawback of being too acidic and of having, in particular in the case of powdered products, a nonhomogeneous appearance after reconstitution, due to coagulation of the milk proteins by the acidity generated during fermentation. They are therefore sometimes poorly accepted by the child and by the mother.

In order to remedy these drawbacks, international application WO 01/01785 has already proposed a method for the production of an immunostimulant milk product by bioconversion, without fermentation and therefore without acidification of the final product, of a milk substrate using bifidobacteria, and in particular the strain *Bifidobacterium breve*, deposited according to the Treaty of Budapest, on May 31, 1999, under the number I-2219, with the CNCM (Collection Nationale de Cultures de Microorganismes) held by the Pasteur Institute, 25 rue du Docteur Roux, in Paris.

However, the method of preparation described in that international application does not make it possible to prepare food products other than milk products and requires conditions for implementation that are restrictive from an industrial point of view, in particular the maintaining of aerobic culture conditions, the maintaining of the culture medium at an osmotic pressure corresponding to water activity (AW) of 0.93 to 0.97, and/or the maintaining of the culture medium at a temperature of between 40 and 48° C.

Moreover, bacteria of the *Bacteroides fragilis* genus represent approximately from 30 to 50% of the flora present in fecal matter in humans. They are located mainly in the colon ($10^{11}$ bacteria per gram of stools). However, in the event of abnormal proliferation, bacteria of the *Bacteroides fragilis* genus are responsible for 80% of anaerobic bacterial infections and are increasingly common due to their increasing resistance to antibiotic treatments. Abnormal proliferation thereof in the organism can result in:

- abscess formation (abdominal abscess, brain abscess, liver abscess, pelvic abscess, lung abscess, spleen abscess),
- septicemia,
- diarrhea, mainly in young children,
- endocarditis,
- peritonitis,
- pneumonia, in particular necrosing pneumonia.

A mortality rate of 60% if no treatment is given for *Bacteroides fragilis* infections has been reported.

It may therefore be advantageous to be able to provide a product that makes it possible to control the proliferation of *Bacteroides fragilis*.

The inventors have therefore developed that which forms the subject of the invention in order to remedy all of the drawbacks exhibited by the products described in the prior art and in order to provide an immunomodulatory product that can be incorporated into any type of food product or can be used for preparing immunomodulatory pharmaceutical compositions.

The inventors have also given themselves the aim of providing a food or pharmaceutical composition that has a regulatory effect on the intestinal microflora, in particular to the detriment of the development of pathogenic bacterial species, in particular *Bacteroides fragilis*.

A first subject of the present invention is therefore an immunomodulatory product, characterized in that it is obtained according to a method of preparation comprising the following steps:

- inoculation and incubation, under aerobic or anaerobic, preferably anaerobic, conditions and at a temperature of between approximately 30 and 40° C., of *Bifidobacterium* comprising at least the strain *Bifidobacterium breve* I-2219 in an aqueous substrate having a pH of between approximately 6 and 8 and comprising at least the following ingredients:
  i) lactoserum permeate,
  ii) a lactoserum protein hydrolyzate,
  iii) lactose,
- removal of the *Bifidobacterium* from the aqueous substrate;
- ultrafiltration of the aqueous substrate through filtration membranes having a cut-off threshold of between 100 and 300 kDa, so as to obtain a concentrated retentate;
- dehydration of the concentrated retentate, preferably by lyophilization;
- dissolution of the dehydrated retentate in a buffer;

gel exclusion chromatography of the retentate solution, on a column having an exclusion threshold of 600 kDa;

recovery of the excluded fraction at the end of the chromatography, which fraction constitutes the immunomodulatory product.

The excluded fraction obtained by carrying out the method in accordance with the invention has immunomodulatory properties; it makes it possible in particular to stimulate the proliferation of *Bifidobacterium* and to decrease the population of *Bacteroides fragilis* in the intestinal flora.

According to the invention, the lactoserum permeate that goes to make up the composition of the aqueous substrate can be in the form of a powder, obtained by ultrafiltration of lactoserum, after drying (by spray drying or by any other drying technique), of the liquid fraction, which may or may not be demineralized, that crosses the membrane during the ultrafiltration of the lactoserum.

The lactoserum protein hydrolyzates that can be used in the context of the present invention can be obtained by the methods normally used for the preparation of protein hydrolyzates, in particular by enzymatic hydrolysis of the lactoserum proteins using proteases such as trypsin, chymotrypsin, etc. Many serum protein concentrates or isolates, along with lactoserum protein hydrolyzates, that are suitable for implementing the invention are known in themselves and are commercially available.

Before its use, the aqueous substrate is preferably filtered through membranes, for example through polyethersulfone membranes having a cut-off threshold of between 100 and 300 kDa, and the permeate is then autoclaved at a temperature of approximately 120° C. for approximately 30 minutes so as to prevent any undesirable bacterial contamination of the culture medium.

Before use, the pH of the aqueous substrate can be adjusted to the desired value using any basifying agent conventionally used by those skilled in the art, such as, for example, sodium hydroxide or potassium hydroxide.

The *Bifidobacterium* bacteria are preferably inoculated into the aqueous substrate in a proportion of $1 \times 10^4$ to $4 \times 10^9$ colony forming units (CFU) per ml of substrate. This inoculation can be carried out, for example, by adding, to the aqueous substrate, in suitable proportions, a frozen concentrate of *Bifidobacterium*, or a preculture on medium for *bifidobacterial* growth.

According to a preferred embodiment of the invention, the pH of the aqueous substrate is maintained at a value of between approximately 6 and 8 throughout the incubation period, and even more preferably between 6.5 and 7.5. The pH is preferably maintained by continuous neutralization of the aqueous substrate using a basifying agent as described above or by means of a diluted (preferably 50/50) ammonia solution.

According to a preferred embodiment of the invention, the temperature of the substrate is maintained at a value of between approximately 37 and 40° C. throughout the incubation period, said period being generally between 10 and 20 hours.

According to a preferred embodiment of the method in accordance with the invention, the ingredients of the aqueous substrate are present in the following amounts:
 i) lactoserum permeate: from approximately 3 to 80 g, and even more preferably from approximately 40 to 60 g,
 ii) lactoserum protein hydrolyzate: from approximately 2 to 80 g, and even more preferably from approximately 5 to 15 g,
 iii) lactose: from approximately 5 to 50 g, and even more preferably from approximately 10 to 30 g,
these amounts being given per liter of said aqueous substrate.

According to a particular embodiment of the invention, the aqueous substrate may also comprise at least one additional ingredient chosen from yeast extracts, buffer salts and cysteine hydrochloride.

When the aqueous substrate comprises a buffer salt, the latter is preferably chosen from sodium dihydrogen phosphate and potassium dihydrogen phosphate, and then preferably represents from approximately 0.5 to 5 g, and even more preferably from approximately 1.5 to 3 g, per liter of aqueous substrate.

When the aqueous substrate comprises a yeast extract, the latter then preferably represents from approximately 0.5 to 5 g, and even more preferably from approximately 1.5 to 3 g, per liter of aqueous substrate.

When the aqueous substrate comprises cysteine hydrochloride, the latter then preferably represents from approximately 100 to 500 mg, and even more preferably from approximately 200 to 400 mg, per liter of aqueous substrate.

At the end of the incubation period, the *Bifidobacterium* can be removed from the culture medium, for example, by microfiltration or by centrifugation of the aqueous substrate. According to a preferred embodiment of the invention, the removal of the *Bifidobacterium* from the culture medium is carried out by centrifugation of the aqueous substrate, for example at a speed of 3000 g for a period of approximately 1 hour.

According to a preferred embodiment of the invention, the method also comprises, after the *Bifidobacterium* removal step, an additional step consisting of destruction of the residual enzymatic activities contained in the aqueous substrate after incubation, for example by thermal treatment thereof at a temperature of approximately 75° C. for approximately 3 minutes.

The aqueous substrate ultrafiltration step is preferably carried out through polyethersulfone membranes, at a temperature less than approximately 60° C.

At the end of the ultrafiltration step, the concentrated retentate thus obtained is preferably washed several times, for example with deionized water, before being finally reconcentrated before being dehydrated, for example by lyophilization.

The buffer used to dissolve the dehydrated retentate is preferably chosen from buffers that have a pH of between 6 and 8, such as, for example, the Tris buffer adjusted to the desired pH by the addition of hydrochloric acid.

The nature of the gels that can be used to perform the exclusion chromatography is not critical provided that said gels have an exclusion threshold of 600 kDa. As gel, use may in particular be made of gels composed of crosslinked agarose and dextran, such as the product sold under the trade name Superdex® 200 by the company Amersham Biosciences.

When the chromatography is finished, the excluded fraction recovered can subsequently be dialyzed against distilled water and then optionally diluted so as to return to the initial concentration of the excluded fraction.

Finally, the excluded fraction constituting the immunomodulatory product can be used directly, or can be frozen or lyophilized for conservation and subsequent use.

This excluded fraction essentially consists of a complex of polysaccharides and of proteins in which the carbohydrate fraction represents approximately from 5 to 30% by weight, the protein fraction representing approximately from 70 to 95% by weight relative to the total weight of said complex.

According to the invention, the carbohydrate fraction of the excluded fraction has the following monosaccharide composition (expressed as molar ratios with respect to rhamnose):

galactose: 5.5 to 8; mannose: 0.8 to 1.3; glucose: 2.5 to 5; N-acetylgalactosamine: 0.3 to 1; N-acetylglucosamine: 0.07 to 0.3; neuraminic acid: 0 to 0.15, and rhamnose: 1.

According to the invention, the protein fraction of the excluded fraction can comprise at least one peptide, obtained by trypsin hydrolysis, corresponding to at least one of the following sequences:

RELGIGTPSFLHNGGQWYIYA (SEQ ID No. 1)
RVLYNPGQYXYVR (SEQ ID No. 2)
EQATANGQVSSGQQSTGGSAAP (SEQ ID No. 3).

A subject of the invention is also the immunomodulatory product obtained according to the method described above, as a medicament, and in particular as an immunomodulatory medicament.

Another subject of the invention is a pharmaceutical composition, characterized in that it contains, as active principle, at least one immunomodulatory product obtained according to the method described above, and at least one pharmaceutically acceptable carrier.

The term "pharmaceutically acceptable" is intended to mean any carrier which, while conserving the properties of the immunomodulatory product obtained according to the method in accordance with the invention, particularly the immunomodulatory properties, makes it possible to transport said product.

The pharmaceutical composition according to the invention may be in any galenic form desired for oral administration to humans or animals, for instance in the form of a liquid for a syrup or a solution, a spray, or in the form of a solid, for instance a powder, a tablet, a gelatin capsule, a capsule or a spray powder, in their various immediate- or programmed-release forms, a gum, a paste or granules, or in any other form suitable for oral administration.

The immunomodulatory product obtained according to the method in accordance with the invention can also be incorporated, as an ingredient, into food compositions.

Consequently, a subject of the invention is also a food composition, characterized in that it contains, as ingredient, at least one immunomodulatory product obtained according to the method in accordance with the invention.

Such food compositions may be intended for human or animal food and may in particular be in the form of a fermented or non-fermented, milk or non-milk preparation, of animal or plant origin, including in particular infant formulas, or for adults and senior citizens, and in particular in the form of an infant milk preparation, of liquid or powdered milk, of fresh products, of cereals, of biscuits (fodder), of jars of baby food, of desserts, etc., or else in the form of food or dietetic products for adults, including products for hospitals, or of nutritional supplements.

The present invention will be understood more clearly from the further description which follows, which refers to examples of preparation of the immunomodulatory product in accordance with the invention, and also to the attached figures in which.

EXAMPLE 1

Preparation of an Immunomodulatory Product Obtained by Culturing *Bifidobacterium*

A culture medium containing the following ingredients is prepared:
50 g/l of lactoserum permeate,
10 g/l of lactoserum protein hydrolyzate,
20 g/l of lactose,
2 g/l of yeast extract,
2.5 g/l of potassium dihydrogen phosphate,
0.3 g/l of cysteine hydrochloride.

The culture medium is ultrafiltered on CENTRAMATE® cassettes sold by the company Pall, equipped with polyethersulfone membranes having a cut-off threshold of 200 kDa, and the permeate is autoclaved for 30 minutes at 120° C. The pH of the culture medium is then adjusted to a value of 6.5 using a solution of ammonia diluted one in four.

The culture medium is then inoculated with the bifidobacteria in a proportion of 6% (v/v) of a frozen concentrate of the CNCM I-2219 *Bifidobacterium breve* strain containing $5 \times 10^{10}$ CFU of bifidobacteria per ml of frozen concentrate. The initial bacterial population is $3 \times 10^{8}$ CFU of *bifidobacteria* per ml of culture medium. The *bifidobacteria* are cultured under conditions of anaerobiosis, at a temperature of between 37 and 40° C. During culturing, the pH of the culture medium is regulated at 6.5 by means of a solution of ammonia diluted one in four. The culturing time is 15 hours and the *Bifidobacterium* population at the end of culturing is approximately $2 \times 10^{7}$ CFU per ml of culture medium.

At the end of culturing, the bacteria are removed from the fermented culture medium by centrifugation for 1 hour at 3000 g. The residual enzymatic activities contained in the centrifugation supernatant are destroyed by thermal treatment at 75° C. for 3 minutes.

The supernatant is ultrafiltered on CENTRAMATE® cassettes sold by the company Pall, equipped with polyethersulfone membranes having a cut-off threshold of 300 kDa, at a temperature of approximately 40° C. It is thus concentrated 3 times, and then washed 3 times with deionized water. During the final wash, a 7-fold concentration of the portion retained by the membrane is carried out. A concentrate called retentate is thus obtained. The retentate is dehydrated by lyophilization, and then taken in a Tris-NaCl buffer at pH 8.

1) Study of the Composition of the Retentate Obtained

The composition of the retentate is studied by exclusion chromatography.

To do this, 25 µl of retentate are injected, at a flow rate of 0.6 ml per minute, onto a column of SUPERDEX® 200 gel sold by the company Amersham Biosciences and having an exclusion threshold of 600 kDa, coupled to a diode array UV-detector (200-300 nm). The signal is integrated using the KROMASYSTEM® 2000 software sold by the company Kontron Instruments. Two fractions are thus separated: a fraction excluded from the gel is eluted after 12.5 minutes starting from the injection, and a filtered fraction is eluted from 16 to 32 minutes starting from the injection.

Figure 1:
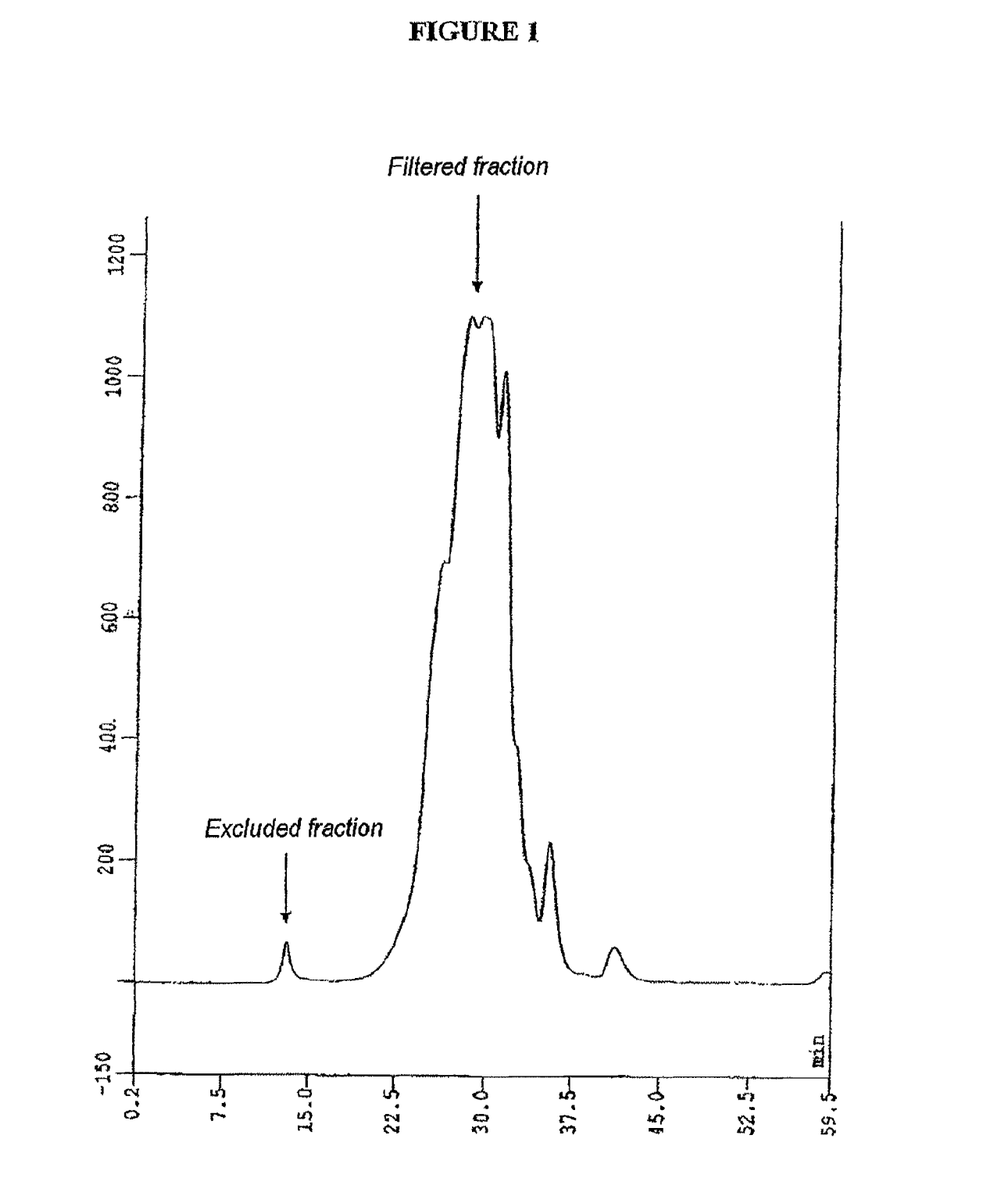
FIG. 1 represents the chromatogram obtained after injection, onto a column filled with a SUPERDEX® 200 gel, of a culture medium fermented for 15 hours with the CNCM I-2219 *Bifidobacterium breve* strain (absorbance in millivolts as a function of elapsed time in minutes)

The results obtained on the retentate after 15 hours of fermentation are reported in the attached FIG. 1, which represents the absorbance (in millivolts) as a function of the elapsed time (in minutes) since the injection of the retentate onto the column. These results represent a typical chromatogram showing the excluded fraction and the filtered fraction of the retentate thus analyzed.

Figure 2:
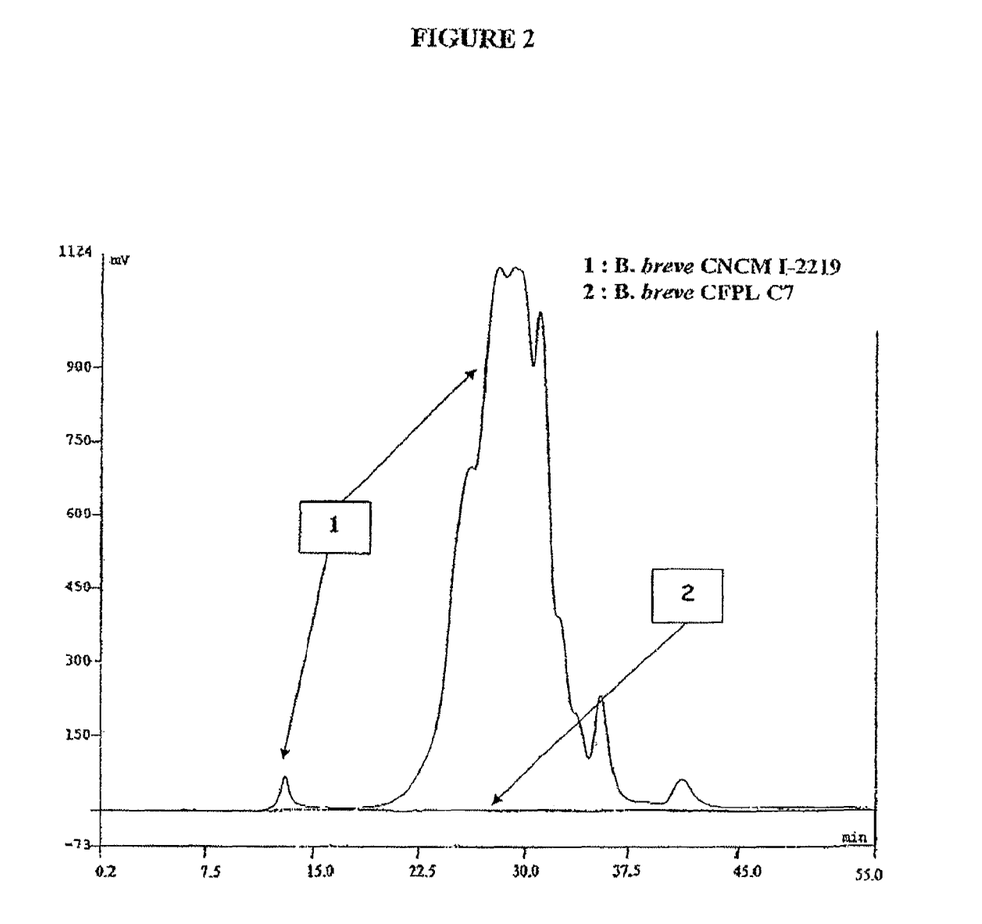
FIG. 2 compares the chromatograms obtained after injection, onto a column filled with a SUPERDEX® 200 gel, of a culture medium fermented with the CNCM I-2219 *Bifidobacterium breve* strain or with the CFPL (Collection de la Faculte de Pharmacie de Lille) C7 *B. breve* strain (absorbance in millivolts as a function of elapsed time in minutes)
Figure 3:
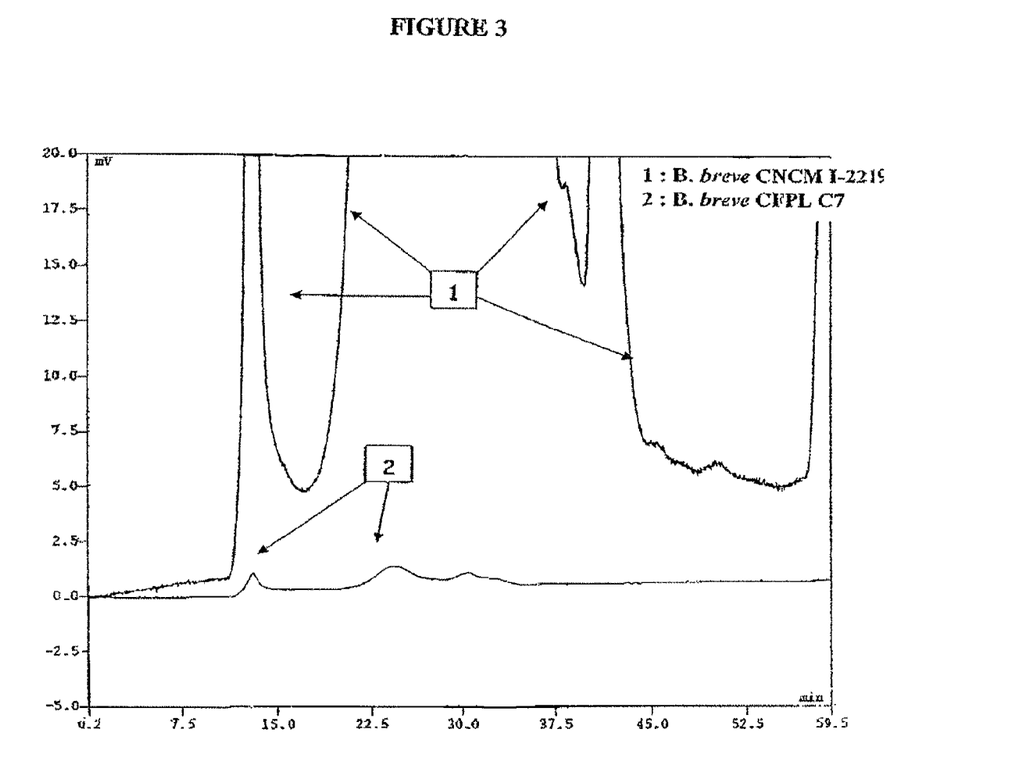
FIG. 3 represents an enlargement of FIG. 2.

FIGS. 2 and 3 represent the chromatograms obtained after analysis of a retentate derived from a culture carried out as described above, and of a retentate derived from a culture carried out under the same conditions but with a different *bifidobacterial* strain (CFPL C7 *B. breve*).

FIG. 2 represents the absorbance (in millivolts) as a function of the time elapsed (in minutes) since the injection onto the column of the retentates corresponding to the two cultures carried out, respectively, with the CNCM I-2219 *B. breve* strain and with the CFPL C7 *B breve* strain. These results show that, contrary to the retentate of the culture carried out with the CNCM I-2219 *B. breve* strain, the chromatogram of the retentate of the culture carried out with the CFPL C7 *B. breve* strain exhibits no peak corresponding to the excluded fraction and to the filtered fraction of the retentate. On the other hand, FIG. 3, which represents an enlargement of FIG. 2, shows that it is necessary to considerably enlarge the absorbance scale of FIG. 2 in order to reveal the excluded fraction and the filtered fraction of the retentate corresponding to the culture carried out with the CFPL C7 *B. breve* strain. These results thus demonstrate that the CFPL C7 *B. breve* strain does not have the potential for active principle production that the CNCM I-2219 *B. breve* strain represents.

2) Preparation of the Excluded Fraction of the Retentate

The concentrated retentate, taken up beforehand in a Tris-NaCl buffer, pH 8, is subjected to preparative chromatography. The separation is carried out by chromatography on a Superdex® 200 gel column sold by the company Amersham Biosciences, 50 mm in diameter and 100 cm high, fed at a flow rate of 5 ml per minute and having an exclusion threshold of 600 kDa. The fractions are collected every 10 ml and the absorbance thereof is measured at 280 nanometers.

Two fractions are thus separated:
a fraction excluded from the gel, having a molecular weight of greater than 600 kDa (retention time of 130 to 180 minutes+/−10%),
a filtered fraction having a molecular weight of between 200 and 600 kDa (retention time of 187 to 370 minutes+/−10%).

The excluded fraction or active part is dialyzed against distilled water and then diluted so as to return to the concentration of the retentate. This fraction can then be conserved in frozen or lyophilized form. The filtered fraction can also be conserved in the same way.

EXAMPLE 2

Analysis of the Carbohydrate and Protein Composition of the Active Part (Excluded Fraction) Prepared from a Culture of *Bifidobacterium*

1) Analysis of the Carbohydrate Composition of the Active Part

The lyophilized powder of excluded fraction as prepared above in Example 1 (10 mg) is taken up with pure anhydrous hydrazine (200-300 microliters). The mixture is incubated at 110° C. overnight, dried under a stream of nitrogen and taken up in 1 ml of water. The solution is then fractionated by gel permeation on a Fractogel TSK column sold under the reference HW40 by the company Merck, and the elution is carried out in water. The presence of sugars in the various fractions collected is sought by the orcinol method and by thin layer chromatography. The results obtained (not represented) show that most of the sugars are in the fraction not retained on the gel (>10 kDa) and do not migrate very far after thin layer chromatography. The carbohydrate part of the excluded fraction therefore constitutes a polysaccharide having a molar mass of greater than 10 kDa. The carbohydrate part of the excluded fraction represents approximately 15 to 20% by mass of the latter.

The molar composition of the carbohydrate fraction of the active part is determined by gas chromatography after methanolysis with a mixture of 0.5 M hydrochloric acid and methanol for 24 hours at 80° C.

Two samples of the excluded fraction (samples 1 and 2 CNCM I-2219: respectively, E1 and E2), originating from two different trials carried out according to example 1, are analyzed.

By way of comparison, the same analyses were carried out on a sample where the CNCM I-2219 *Bifidobacterium breve* strain has been replaced with the CFPL C7 *Bifidobacterium breve* strain (sample C7) cultured under the same conditions, and also on a sample where the CNCM I-2219 *Bifidobacterium breve* strain has been cultured on a lactose medium not in accordance with the invention (lactose medium sample: ML) having the following composition:
60 g/l of lactose,
2 g/l of yeast extract,
0.3 g/l of cysteine hydrochloride,
the subsequent extract and purification steps being comparable in all respects to those described above.

The molar ratios of given monosaccharides (expressed with respect to rhamnose) obtained for the excluded fraction of these various samples are given in Table I below:

TABLE I

|  | E1 | E2 | C7* | ML.* |
| --- | --- | --- | --- | --- |
| Galactose | 6.50 | 7.60 | 2.00 | 3.80 |
| Mannose | 0.92 | 1.10 | 2.70 | 6.20 |
| Glucose | 3.20 | 4.30 | 3.50 | 2.70 |
| N-acetylgalactosamine | 0.80 | 0.47 | 1.00 | 0.10 |
| N-acetylglucosamine | 0.17 | 0.10 | 0.38 | 0.10 |
| Neuraminic acid | 0.08 | — | 0.49 | — |
| Rhamnose | 1.00 | 1.00 | 0 | 1.00 |

*comparative sample that is not part of the invention

It may be noted that there is an absence of rhamnose in the sample C7 where the CNCM I-2219 *Bifidobacterium breve* strain has been replaced with the CFPL C7 *Bifidobacterium breve* strain. It may also be noted that the distribution of sugars between the samples E1 and E2 is different from that of the sample ML corresponding to the CNCM I-2219 *Bifidobacterium breve* strain cultured on a lactose medium not in accordance with the invention. In particular, the samples E1 and E2 contain more galactose and more N-acetylgalactosamine than the sample ML, and less mannose than the sample ML.

2) Analysis of the Protein Composition of the Active Part

The protein fraction of the active part represents approximately 80 to 85% by mass of the latter.

Sequencing of the protein part of the active part is carried out after a proteolysis step using a 1% solution of trypsin in a 0.1 M Tris buffer, at pH 8.5, as described in the article Rosenfeld J. et al., Analytical Biochemistry, 1992, 203, 173-179.

The peptides are purified by reverse-phase HPLC on an Ultrasphere® ODS (octadecylsilane) column 2 mm in diameter and 200 mm in length, sold by the company Beckmann. Elution is carried out with a linear gradient of acetonitrile in a 0.1% trifluoroacetic acid solution.

The isolated peptides are sequenced (according to the method described in the article by Rosenfeld J. et al., mentioned above) on a Procise 492 reference device sold by the company Perkin-Elmer.

The sequences are then compared with those contained in the following databases: GenBank CDS translation, PDB (Protein Data Bank), SwissProt, PIR (Protein Information Resource), PRF (Protein Research Foundation), using the NCBI (National Center for Biotechnology Information) BLAST 2.2 program (Basic Local Alignment Search Tool).

This analysis made it possible to show that the protein fraction of the active part consists mainly of peptides of the milk medium (lactoferrin, beta-lactoglobulin, serum albumin, etc.), of a part that exhibits good homology (minimum of 60%) with a *Bifidobacterium longum* protein sequence (RELGIGTPSFLHNGGQWYIYA (SEQ ID No. 1)) and of a part for which it was not possible to determine any significant homology with known sequences, and which has the following sequences:

```
RVLYNPGQYXYVR              (SEQ ID No. 2)

EQATANGQVSSGQQSTGGSAAP.    (SEQ ID No. 3)
```

EXAMPLE 3

Study of the Immunomodulatory Activity of the Excluded Fraction of the Retentate 1) Effect of the Excluded Fraction on the Intestinal Flora of Mice The effect of the excluded fraction (active part), obtained according to the method described above in example 1, on the evolution of the intestinal flora of mice was studied.

The test was carried out on male C3H mice, which are second-generation mice of a line of axenic animals, in which an adult human intestinal flora is implanted (originating from the CDTA, Centre de Distribution, Typage & Archivage animal, CNRS, Orléans, France).

The mice are maintained in isolators in order to prevent any modification of their novel intestinal flora. The mice are 8-10 weeks old when they are received. The mice are given an adaptation time of at least 2 weeks after reception in order to eliminate any stress due to the transport and so that they acclimatize to their new environment.

Throughout this adaptation period and up until the beginning of the experiment, these mice have sterile water to drink.

Throughout the time of the experiment, the food used as food base is a standard diet of RO3 granules sold by the company UAR, sterilized by irradiation, containing 25% of proteins, 49.8% of carbohydrates, 5% of lipids and 4% of cellulose.

During the 21 days of the trial, the water in the bottles is replaced with the various products to be tested, i.e. the filtered fraction and the excluded fraction, in a proportion of 6 ml per day and per mouse. A daily bottle change is carried out in order to prevent any modification of the composition of the products to be tested by bacterial proliferation. The stools are collected for analysis before the treatment (T0), and then on the 7th, on the 15th and on the 21st day during administration of the product (T7, T15 and T21).

Each product is tested on a batch of at least 6 mice, and the evolution of *Bifidobacterium* and *Bacteroides fragilis* bacteria in the intestinal flora of the mice is followed.

The stool samples are made in sterile hemolysis tubes and are weighed aseptically and then diluted in prereduced Ringer solution diluted one in four and supplemented with cysteine hydrochloride (0.3 g/l), so as to obtain ten-fold dilutions ranging from $10^{-1}$ to $10^{-4}$. The content is finally deposited, in a proportion of 100 µl per dish, onto various culture media contained in Petri dishes:

Beerens (Be) medium (composed of 35 g/l of Columbia agar base, 5 g/l of glucose, 0.3 g/l of cysteine hydrochloride, 0.5% of propionic acid and adjusted to pH 5) for searching for and counting *Bifidobacterium*, after plating out of dilutions ranging from $10^{-1}$ to $10^{-4}$;

*Bacteroides* Bile Esculin (BBE) medium (composed of 37 g/l of tryptone, 32 g/l of Bile Esculin Agar (DIFCO), 0.5 g/l of esculin, 0.5 g/l of ammoniacal iron citrate, 0.2% of a 5 mg/ml solution of hemine, 0.25% of a 40 mg/ml solution of gentamycin and 10 g/l of agar; adjusted to pH 7 and autoclaved at 120° C. for 15 minutes) for searching for and counting *Bacteroides fragilis*, after plating out of dilutions ranging from $10^{-1}$ to $10^{-3}$.

The plating out is carried out using sterile glass beads on the media indicated and the media are read after incubation for 5-7 days under conditions of anaerobiosis at 37° C.

Identification of the bacteria is carried out, firstly after description of the colonies obtained on each of the media and, secondly, using Gram-staining.

The results regarding the evolution of *Bifidobacterium* and of *Bacteroides fragilis* in the stools of the mice are reported respectively in Tables II and III below:

TABLE II

| | *Bifidobacterium* | | | |
|---|---|---|---|---|
| | T0 | T7 | T15 | T21 |
| Filtered fraction | 3.8 ± 0.5 (9) n = 18 | 4.3 ± 0.55 (11) n = 18 | 4.75 ± 1.15 (9)* n = 18 | nd — |
| Excluded fraction | 4.02 ± 0.74 (8) n = 18 | 4.54 ± 1.0 (11) n = 18 | 4.56 ± 0.36 (12)* n = 12 | 4.76 ± 0.27 (6)* n = 6 | nd: not determined,
*p < 0.025

TABLE III

| | *Bacteroides fragilis* | | | |
|---|---|---|---|---|
| | T0 | T7 | T15 | T21 |
| Filtered fraction | 4.4 ± 0.7 (15) n = 18 | 4.4 ± 0.5 (12) n = 18 | 4.3 ± 0.7 (12) n = 18 | 4.1 ± 0.9 (7) n = 12 |
| Excluded fraction | 4.28 ± 0.35 (18) n = 18 | 3.99 ± 0.37 (8) n = 18 | 3.74 ± 0.28 (9) n = 12 | 3.2 ± 0.16 (4)** n = 6 | nd: not determined,
*p < 0.025;
**p < 0.05

In these tables, the results obtained are expressed as mean and standard deviation of the log of the number of CFU/g of stools, and n is the number of mice used for each product and days tested. (Wilcoxon rank test for comparing paired samples); the asterisks indicate the significant results with respect to time T0. In these tables, the figure given between parentheses corresponds to the number of mice in which the bacterium in question is present above the detection threshold. The results corresponding to the non-inoculated medium are similar to the value obtained at T0 and remain constant over time for the 21 days of the experiment (results not represented in the tables).

These results show that the administration of either one of the two fractions (excluded or filtered) effectively results in an increase in *Bifidobacterium*, but that only the excluded fraction is effective for bringing about a decrease in the population of *Bacteroides fragilis* in the intestinal flora of the mice.

2) Effect of the Excluded Fraction on the Regulation of Intestinal Translocation of the Microorganisms The measurement of intestinal translocation of the microorganisms in the mouse is carried out on male mice of the C3H line with adult human flora (breeding colony at the CDTA-CNRS, Orléans, France). Throughout the adaptation period and up to the beginning of the experiment, these mice have sterile water to drink.

Throughout the duration of the experiment, these mice will be fed with RO3 granules sterilized by radiation.

At 10-12 weeks old, the beginning of the experiment, three groups are formed, a group of 18 mice that will receive, throughout the duration of the experiment, the excluded fraction of CNCM I-2219 *Bifidobacterium breve* metabolites in place of water in the bottles, at a rate of 8-10 ml per day and per mouse, while two other groups of 12 and 23 mice will, respectively, receive the filtered fraction or will continue to receive sterile water (control group).

On the 21st day, a stool sample is taken as described above and the mice are sacrificed in order to perform a bacteriological study.

Two types of data are obtained from the analysis of the organs of the sacrificed mice:

translocation by target organ, i.e. evaluation of the number of mice in which the target organ is contaminated and of the percentage of the population exhibiting contamination of the target organ;

bacterial dissemination, i.e. the intensity of bacterial dissemination represented by the number of positive organs and also the number of mice and the percentage of the population exhibiting dissemination of a given intensity.

In order to remove the organs to be analyzed, the animal is removed from the isolator, transferred under aseptic conditions under a laminar flow hood, and sacrificed by chloroform inhalation.

The skin is decontaminated with 70° alcohol, and then, for each mouse, the organs are removed aseptically in the following order: blood from the heart, lung, liver, spleen and kidney. In order to evaluate the weight thereof, a fraction of each organ is suspended in 9 ml of Ringer solution (diluted one in four, supplemented with cysteine hydrochloride (0.3 g/l) and regenerated in boiling water for 15 minutes). The organs are then ground using a "Pastette®" single-use sterile Pasteur pipette, sold by the company VWR, or a "Liquipette®" single-use Pasteur pipette sold by the company Gosselin. 100 µl of the stock suspension and of the 10-fold dilution thereof are then plated out, using sterile glass beads, on Columbia agar (sold by the company Beckton-Dickinson), supplemented with glucose (5 g/l), with cysteine hydrochloride (0.3 g/l) and with horse blood (5% v/v, sold by the company Eurobio). After incubation under conditions of anaerobiosis for 7 days at 37° C., each colony type is counted and the morphology of the bacteria is then determined after Gram-staining.

The results obtained, relating to the analysis of translocation by target organ, are given in Table IV below:

TABLE IV

| Target organ | Control group | Filtered fraction | Excluded fraction | p[c] |
|---|---|---|---|---|
| Kidney | 12[a] (52.2)[b] | 8 (66.7) | 7 (38.9) | NS |
| Spleen | 13 (56.5) | 9 (75.0) | 3 (16.7)* | P < 0.01 |
| Liver | 10 (43.5) | 8 (66.7) | 5 (27.8) | NS |
| Lung | 11 (47.8) | 7 (58.3) | 2 (11.1)* | P < 0.02 |

[a]= number of mice in which the target organ is contaminated
[b]= percentage of the population exhibiting contamination of the target organ
[c]= comparison of the groups having consumed one of the products, relative to the control group, using Fisher's exact test.
The group exhibiting a significant difference is marked with an asterisk *.

The results thus obtained show that the spleen and the lung are less frequently contaminated in the population for which the drinking water was substituted with the excluded fraction than in the control population of mice that received water to drink.

Furthermore, these results reveal that the filtered fraction has no effect on the regulation of bacterial translocation.

The results obtained regarding bacterial dissemination are given in Table V below:

TABLE V

| Intensity of dissemination | Control group | Filtered fraction | Excluded fraction | p[d] |
|---|---|---|---|---|
| Weak (0-1)[a] | 8[b] (35)[c] | 3 (25) | 12 (66.7)* | P < 0.043 |
| Medium (2) | 4 (17) | 1 (8.3) | 5 (27.8) | NS |
| Strong (3-4) | 11 (48) | 8 (66.7) | 1 (5.5)* | P < 0.004 |

[a]= intensity of bacterial dissemination represented (between parentheses) by the number of positive organs,
[b]= number of mice exhibiting dissemination of a given intensity,
[c]= percentage of the population exhibiting dissemination of a given intensity,
[d]= comparison of the groups having consumed one of the products, relative to the control group, using Fisher's exact test.
The group exhibiting a significant difference is marked with an asterisk *.

The number or mice exhibiting less than one contaminated organ (weak intensity of dissemination) is higher in the population for which the drinking water was substituted with the excluded fraction than in the control population of mice having received water to drink.

In addition, the number of mice exhibiting at least three contaminated organs (strong intensity of dissemination) is lower in the population for which the drinking water was substituted with the excluded fraction than in the control population of mice having received water to drink.

It is therefore noted that the bacterial dissemination is less intense in the mice having received drinking water supplemented with the excluded fraction. In this case, the regulation of bacterial translocation is more effective.

3) Effect of the Excluded Fraction on the Expression of Galectin-1 and Galectin-3

The measurement of the expression of galectin-1 and of galectin-3 is carried out on the mice with adult human flora described above.

At 12-14 weeks old, the beginning of the experiment, two groups of mice are formed, one group of mice which will receive, throughout the duration of the experiment, the excluded fraction containing the CNCM I-2219 *Bifidobacterium breve* metabolites in place of water in the bottles, at a rate of 10 ml per day and per mouse, while another group of mice will continue to receive water (control group).

On the 7th, 15th and 21st days, a batch of mice is sacrificed in order to perform a biological study on the expression of galectin-1 and of galectin-3, evaluated by assaying the mRNA encoding these galectins by quantitative RT-PCR (polymerase chain reaction). The organs removed from the mice of the control group, sacrificed on the 7th, 15th and 21st day, were grouped together by organ in order to constitute a pool used as a control throughout the duration of the experiment.

The modification of the expression of galectin-1 and of galectin-3 in the organs tested constitutes an indicator of the effect of the metabolites produced by the CNCM I-2219 *Bifidobacterium breve* strain contained in the excluded fraction.

Galectin-1 and galectin-3 are assayed in the spleen and lungs of mice having been sacrificed as described above.

To do this, a fraction of lung (a lobe) and half the spleen are removed sterilely and in this order from each mouse. The fragments are then placed in Petri dishes treated beforehand for 24 hours with a sterile solution of water and DEPC (Di-Ethyl PyroCarbonate, sold by the company Sigma) at 1/1000. The organs are then perfused for a first time with PBS buffer using a sterile syringe and needle in order to eliminate the blood therefrom. The organs are then transferred into another Petri dish containing 200 microliters of PBS to which 50 units of RNase inhibitor (sold by the company Applied Biosystems) had been added, and are perfused again with this solution. The organs are finally cut up into slices of less than 5 mm, which are placed in a Biopur® tube (Eppendorf) containing 0.5 ml of an RNA-stabilizing solution, sold under the reference RNALater® by the company Qiagen. The organs are then stored in the freezer at −20° C. until the analysis.

a) Extraction of Total RNA from the Organs Removed

The total RNA is extracted from the tissues after cell lysis according to the protocol for using the RNeasy protect® extraction kit sold under the reference 74126 by the company Qiagen.

To do this, the stabilizing solution is removed and a tungsten bead treated with DEPC and also 600 microliters of a lysis solution (RLT buffer contained in the kit) are added to each organ. They are then ground using a Retsch MM2000 mill, and then centrifuged at 13 000 g for 3 minutes at 4° C. The supernatant is then placed in a 1.5 ml tube containing 600 microliters of 70% ethanol, and then homogenized. Part of this solution (700 microliters) is then loaded onto a filtration column which makes it possible to attach the RNAs, so as to be centrifuged at 8000 g for 1 minute at 4° C. After having emptied the collecting tube, 700 microliters of a washing buffer (RW1 buffer contained in the kit) are added to the column, which is then centrifuged at 8000 g for 1 minute at 4° C. The collecting tube is again emptied and 500 microliters of a second washing buffer containing 70% ethanol (RPE buffer contained in the kit) is added to the column so as to be centrifuged at 8000 g for 1 minute at 4° C. The latter step is repeated, but by performing a centrifugation at 13 000 g for 2 minutes at 4° C. Finally, 30 microliters of an elution buffer for detaching the RNAs from the column (RNase free buffer contained in the kit) are added to the column. The eluate is then centrifuged at 8000 g for 1 minute at 4° C. after having been incubated at ambient temperature for 5 minutes. The elution step is again performed and the samples thus obtained are rapidly frozen at −80° C.

An amount equivalent to one unit of DNase, sold by the company Boehringer, is added to each sample, which is then incubated in a water bath at 37° C. for 15 minutes.

In order to evaluate the amount of total RNA in the samples, the latter are diluted to ⅛th in sterile water, and the dilution is placed in a microcuvette for reading the absorbance at 260 nm on a Genquant reference UV spectrophotometer, sold by the company Pharmacia. In order to obtain the concentration of total RNA in the samples, the optical density (OD) value thus obtained is multiplied by the dilution factor and by 40 (one OD unit=40 micrograms/ml of RNA).

b) Quantitative RT-PCR Using the Taq Man® Methodology

The Quantitative RT-PCR is Carried Out Using the qPCR™ Core Kit sold by the company Eurogentec in an Abi Prism 7700 reference thermocycler (Sequence Detection System, Applied Biosystems) sold by the company Perkin Elmer. The reaction mixture summarized in Table VI below is prepared:

TABLE VI

| Reagents | Volume in µl/tube | Final concentration |
| --- | --- | --- |
| PCR buffer (10 x)* | 5 | 1 x |
| MgCl$_2$ (50 mM)* | 5 | 5 mM |
| dNTP (2.5 mM)* | 6 | 300 µM |
| Sense primer (10 pM) | 1 | 200 µM |
| Antisense primer (10 pM) | 1 | 200 µM |
| Probe (10 pM) | 1 | 200 µM |
| RNase inhibitor (40 units) | 0.5 | 20 units |
| Hot Gold Star polymerase (5 units) | 0.25 | 1.25 units |
| MuLV (5 units) | 0.25 | 12.5 units |
| Total RNA | 10 | 100 ng/tube |
| Pure water | qs 50 µl | |

*product provided in the qPCR ™ Core Kit

The reaction mixture is subjected to the following program: 10 minutes at 65° C. in order to eliminate the secondary structures of the RNAs, 30 minutes at 42° C. in order to activate the reverse transcriptase, 10 minutes at 95° C. in order to activate the polymerase, 15 seconds at 95° C. in order to denature the DNA strands and 1 minute at 61° C. for the hybridization and the elongation from the primers. Forty cycles are performed for the last two steps.

The expression of galectin-1 and of galectin-3 is evaluated with respect to the expression of a reference gene, such as that encoding β-actin, the expression of which is constant.

The probes and the primers used and chosen by means of the Primer Express® program sold by the company Perkin Elmer are as follows:

```
Galectin-1:
Sense:
5'-TCA ATC ATG GCC TGT GGT CTG-3'    (SEQ ID No. 4)

Antisense:
5'-AAG CTC TTG GCG TCC GAG G-3'      (SEQ ID No. 5)

Probe:
5'-TCG CCA GCA ACC TGA ATC AAC       (SEQ ID No. 6)
CTG-3'

Galectin-3:
Sense:
5'-AAT GGC AGA CAG CTT TTC G-3'      (SEQ ID No. 7)

Antisense:
5'-GAT CAT GGC GTG GTT AGC-3'        (SEQ ID No. 8)

Probe:
5'-TTC CAC TTT AAC CCC CGC TTC AAT   (SEQ ID No. 9)
GAG AAC-3'

β-actin
Sense:
5'-TGG CGC TTT TGA CTC AGG ATT-3'    (SEQ ID No. 10)
```

-continued

Antisense:
5'-GGG ATG TTT GCT CCA ACC AAC-3'   (SEQ ID No. 11)

Probe:
5'-GCC GTC GCC TTC ACC GTT CCA GTT   (SEQ ID No. 12)

TTT-3'.

In order to validate each microplate subjected to the PCR cycles, a calibrator is prepared from organs from a batch of six C3H mice with human flora subjected to a standard diet (sterile water and RO3 granules) from which the lungs and the spleen have been removed. The total RNAs of each organ were extracted using the protocol described above for the organs of the batches of test mice. The various extracts thus obtained are then combined for each organ in order to constitute a pool used as a calibrator throughout the duration of the analysis.

During the analysis, the samples to be tested are deposited in duplicate and the standard range prepared from the calibrating sample is deposited in triplicate. A mean is then determined from each sample and for the calibrating sample.

The results of the relative expression of galectin-1 with respect to β-actin are given in Table VII below:

TABLE VII

| | | Diet | | |
| | | | Excluded fraction | |
| Organ | Control | 7 d | 15 d | 21 d |
| --- | --- | --- | --- | --- |
| Spleen | n = 17[a]<br>2.78[b]<br>(1.6-3.47)[c] | n = 6<br>1.15 (0.72-1.36)<br>U = p < 0.002<br>bilateral test | n = 6<br>4.5 (3.76-6.92)<br>U = 7 p < 0.002<br>bilateral test | n = 3<br>12.51 (9.68-13.74)<br>U = 0 p < 0.002<br>bilateral test |
| Lung | n = 16<br>1.145<br>(0.69-1.93) | n = 6<br>0.8 (0.56-1.08)<br>U = 17.5 p < 0.05<br>bilateral test | n = 4<br>1.72 (1.67-1.88)<br>U = 5 p < 0.02<br>bilateral test | n = 6<br>1.465 (0.86-1.77) |

The results of the relative expression of galectin-3 with respect to β-actin are given in Table VIII below:

TABLE VIII

| | | Diet | | |
| | | | Excluded fraction | |
| Organ | Control | 7 d | 15 d | 21 d |
| --- | --- | --- | --- | --- |
| Lung | n = 16[a]<br>1295[b]<br>(0.56-2.26)[c] | n = 6<br>1.04 (0.86-1.16) | n = 3<br>0.76 (0.41-1)<br>U = 8 p < 0.05<br>unilateral test | n = 6<br>0.91 (0.75-1.31) |

In Tables VII and VIII:
[a] = number of mice per batch;
[b] = median of the relative expression of galectin
[c] = extreme results of relative expression of galectin;
the value denoted by the letter U is the statistical value of the Mann-Whitney U test;
p indicates the threshold of significance of the method.

These results show that an increase in the expression of galectin-1 is observed in the spleen of the mice for which the drinking water was substituted with the excluded fraction. The expression of galectin-1 (induction of cellular apoptosis, in particular of activated T lymphocytes) in the control animals is twice as high compared with that of actin, which seems to relate to the bacterial contamination of the organ (the expression of galectin-1 is significantly lower in the absence of bacteria in the spleen—U=15, p<0.05—and it increases as a function of the amount of bacterial contamination when bacteria are present—correlation r=0.77, p<0.05, Spearman test). The expression of galectin-1 normalizes after the excluded fraction has been taken for 7 days, and then subsequently increases by a factor of 4 to 10 respectively after 15 and 21 days of taking said fraction (independently of the residual bacterial contamination of the organ). In the lungs, the relative expression of galectin-1 is normal in the control mice and the small but significant decrease after taking the excluded fraction for 7 days is followed by an increase (transiently significant after taking said fraction for 15 days) and then by normalization of the expression of galectin-1 after the excluded fraction has been taken for 21 days.

These results also show that a decrease in the expression of galectin-3 is observed in the lungs of the mice for which the drinking water was substituted with the excluded fraction.

All these results demonstrate that the excluded fraction (immunomodulatory product obtained according to the method in accordance with the invention) has an immunomodulatory effect and makes it possible to increase the population of *Bifidobacterium* and to decrease the population of *Bacteroides fragilis*.

The invention claimed is:

1. An immunomodulatory product obtained according to a method of preparation comprising the following steps: inoculation and incubation, under aerobic or anaerobic conditions and at a temperature of between approximately 30 to 40° C., of Bifidobacterium comprising at least the Bifidobacterium breve strain deposited under the number I-2219 with the CNCM (Collection Nationale de Cultures de Microorganisms in Paris, France) in an aqueous substrate having a pH of between approximately 6 and 8 and comprising at least the following ingredients: i) lactoserum permeate, ii) a lactoserum protein hydrolyzate, iii) lactose, removal of the intact Bifidobacterium from the aqueous substrate; ultrafiltration of the aqueous substrate through filtration membranes having a cut-off threshold of between 100 and 300 kDa, so as to obtain a concentrated retentate; dehydration of the concentrated retentate; dissolution of the dehydrated retentate in a buffer; gel exclusion chromatography of the retentate solution, on a column having an exclusion threshold of 600 kDa; recovery of the excluded fraction at the end of the chromatography, which fraction constitutes the immunomodulatory product, and wherein the excluded fraction at the end of the chromatography is characterized by the absence of intact Bifidobacterium cells.

2. The immunomodulatory product as claimed in claim 1, wherein the Bifidobacterium bacteria are inoculated into the aqueous substrate in a proportion of $1 \times 10^4$ to $4 \times 10^9$ colony forming units per ml of substrate.

3. The immunomodulatory product as claimed in claim 1 wherein the temperature of the substrate is maintained at a value of between 37 and 40° C. throughout the incubation period.

4. The immunomodulatory product as claimed in claim 1, wherein the pH of the aqueous substrate is maintained at a value of between 6 and 8 throughout the incubation period.

5. The immunomodulatory product as claimed in claim 4, wherein the pH of the aqueous substrate is maintained at a value of between 6.5 and 7.5 throughout the incubation period.

6. The immunomodulatory product as claimed in claim 1, wherein the ingredients of the aqueous substrate are present in the following amounts:

i) lactoserum permeate: from 3 to 80 g,
ii) lactoserum protein hydrolyzate: from 2 to 80 g,
iii) lactose: from 5 to 50 g,
these amounts being given per liter of said aqueous substrate.

7. The immunomodulatory product as claimed in claim 6, wherein the ingredients of the aqueous substrate are present in the following amounts:
i) lactoserum permeate: from 40 to 60 g,
ii) lactoserum protein hydrolyzate: from 5 to 15 g,
iii) lactose: from 10 to 30 g,
these amounts being given per liter of said aqueous substrate.

8. The immunomodulatory product as claimed in claim 1, wherein the aqueous substrate also comprises at least one additional ingredient selected from the group consisting of buffer salts, yeast extracts and cysteine hydrochloride.

9. The immunomodulatory product as claimed in claim 8, wherein the aqueous substrate comprises a buffer salt selected from the group consisting of sodium dihydrogen phosphate and potassium dihydrogen phosphate, which represents from 0.5 to 5 g per liter of aqueous substrate.

10. The immunomodulatory product as claimed in claim 8, wherein the yeast extract represents from 0.5 to 5 g per liter of aqueous substrate.

11. The immunomodulatory product as claimed in claim 8, wherein the cysteine hydrochloride represents from 100 to 500 mg per liter of aqueous substrate.

12. The immunomodulatory product as claimed in claim 1, wherein the removal of the intact *Bifidobacterium* from the culture medium is carried out by microfiltration or by centrifugation of the aqueous substrate.

13. The immunomodulatory product as claimed in claim 12, wherein the removal of the intact *Bifidobacterium* from the culture medium is carried out by centrifugation of the aqueous substrate.

14. The immunomodulatory product as claimed in claim 1, wherein the method also comprises, after the step of removing the intact *Bifidobacterium*, an additional step consisting of destruction of the residual enzymatic activities contained in the aqueous substrate after incubation.

15. The immunomodulatory product as claimed in claim 1, wherein the exclusion chromatography is carried out on a crosslinked agarose and dextran gel.

16. The immunomodulatory product as claimed in claim 1, wherein the excluded fraction essentially consists of a complex of polysaccharides and of proteins in which the carbohydrate fraction represents from 5 to 30% by weight, the protein fraction representing from 70 to 95% by weight relative to the total weight of said complex.

17. The immunomodulatory product as claimed in claim 16, wherein the carbohydrate fraction of the excluded fraction has the following monosaccharide composition (expressed as molar ratios with respect to rhamnose): galactose: 5.5 to 8; mannose: 0.8 to 1.3; glucose: 2.5 to 5; N-acetylgalactosamine: 0.3 to 1; N-acetylglucosamine: 0.07 to 0.3; neuraminic acid: 0 to 0.15, and rhamnose: 1.

18. The immunomodulatory product as claimed in claim 16, wherein the protein fraction comprises at least one peptide corresponding to at least one of the following sequences:

| | |
|---|---|
| RELGIGTPSFLHNGGQWYIYA | (SEQ ID No. 1) |
| RVLYNPGQYXYVR | (SEQ ID No. 2) |
| EQATANGQVSSGQQSTGGSAAP. | (SEQ ID No. 3) |

19. A medicament comprising the immunomodulatory product as claimed in claim 1.

20. An immunomodulatory medicament comprising the immunomodulatory product as claimed in claim 1.

21. A pharmaceutical composition, containing, as active principle, the immunomodulatory product obtained according to the method as defined in claim 1, and at least one pharmaceutically acceptable carrier.

22. The pharmaceutical composition as claimed in claim 21, wherein it is intended for oral administration and in that it is in the form of a liquid or of a solid.

23. A food composition, containing, as an ingredient, at least one immunomodulatory product obtained according to the method as defined in claim 1.

24. The food composition as claimed in claim 23, wherein the composition is in a form of a fermented or non-fermented, milk or non-milk preparation, of animal or plant origin, including infant formulas, or for adults or senior citizens.

25. The food composition as claimed in claim 24, wherein the composition is in a form of liquid or powdered milk, of fresh products, of cereals, of biscuits, of jars of baby food, of desserts, of products for hospitals, of dietetic products or of nutritional supplements.

\* \* \* \* \*

UNITED STATES PATENT AND TRADEMARK OFFICE
CERTIFICATE OF CORRECTION

| | |
|---|---|
| PATENT NO. | : 8,197,826 B2 |
| APPLICATION NO. | : 10/552957 |
| DATED | : June 12, 2012 |
| INVENTOR(S) | : Valérie Petay et al. |

It is certified that error appears in the above-identified patent and that said Letters Patent is hereby corrected as shown below:

In Claim 1, at Column 19, line 51, delete "30 to 40°" and replace it with --30 and 40°--.

Signed and Sealed this
Eighteenth Day of September, 2012

David J. Kappos
*Director of the United States Patent and Trademark Office*